United States Patent
Heinzen et al.

(10) Patent No.: US 6,458,296 B1
(45) Date of Patent: Oct. 1, 2002

(54) METHOD AND DEVICE FOR CAPSULATING MICROBIAL, PLANT AND ANIMAL CELLS OR BIOLOGICAL AND CHEMICAL SUBSTANCES

(75) Inventors: Christoph Heinzen, Boniswil; Raphael Plüss-Wenzinger, Schiers; Fritz Widmer, Gockhausen; Harry Brandenberger, Elgg, all of (DE)

(73) Assignee: Inotech AG, Dottikon (DE)

( * ) Notice: Subject to any disclaimer, the term of this patent is extended or adjusted under 35 U.S.C. 154(b) by 0 days.

(21) Appl. No.: 09/623,436
(22) PCT Filed: Jan. 14, 1999
(86) PCT No.: PCT/EP99/00162
§ 371 (c)(1),
(2), (4) Date: Oct. 26, 2000
(87) PCT Pub. No.: WO99/44735
PCT Pub. Date: Sep. 10, 1999

(30) Foreign Application Priority Data

Mar. 7, 1998 (DE) .......................... 198 09 965

(51) Int. Cl.$^7$ .......................... B29B 9/00; B32B 19/02
(52) U.S. Cl. .................. 264/9; 264/4; 264/10; 264/11; 425/5; 428/402.2; 428/402.24; 428/407
(58) Field of Search .................. 264/4, 9, 10, 11; 425/5; 428/402.2, 402.24, 407

(56) References Cited

U.S. PATENT DOCUMENTS 4,302,166 A  11/1981  Fulwyler et al.
4,981,625 A  1/1991  Rhim et al.

FOREIGN PATENT DOCUMENTS

DE  2725849  12/1978
WO  WO96/28247  9/1996

OTHER PUBLICATIONS

Patent Abstracts of Japan, vol. 018, No. 476 (C–1246), Sep. 6, 1994 & JP 06 154587 A (Freunt Ind Co Ltd), Jun. 3, 1994.

Primary Examiner—Samuel A. Acquah
(74) Attorney, Agent, or Firm—Bachman & LaPointe, P.C.

(57) ABSTRACT

The invention relates to a method for capsulating microbial, plant and animal cells or biological and chemical substances, using a nozzle to obtain small, especially spherical particles by vibrating an immobilisation mixture. According to said method, the immobilisation mixture, especially a laminar fluid jet taking the form of an immobilisation mixture, is divided into equal parts by superimposition of an external vibration. In a device especially well suited to carry out this method a metallic counter-element (18) which is mounted down-stream from the nozzle (16) at a distance (a) to, and on the outside of, the nozzle axis (A) is connected to a high-voltage source (30). The counter-element is to be embodied by a metal ring (18) through whose through hole (20) the nozzle axis (A) extends. The metal ring (18) is radially connected to an insulated support (22, 24).

12 Claims, 3 Drawing Sheets

METHOD AND DEVICE FOR CAPSULATING MICROBIAL, PLANT AND ANIMAL CELLS OR BIOLOGICAL AND CHEMICAL SUBSTANCES

The invention concerns a method and an apparatus for encapsulating microbial, vegetable and animal cells or biological and chemical substances through a nozzle to obtain small, substantially spherical particles.

The encapsulation of microbial, vegetable and animal cells and biological and chemical substances—such as catalysts—is of great significance in particular in biotechnology and medicine for immobilisation purposes. In medicine, encapsulation additionally serves to provide a screening effect from the immune system. By virtue of the immobilisation effect, it is possible for the cells or the catalyst to be retained in the process and for the product to be harvested at the same time. That permits use over a prolonged period of time and affords an increased space-time yield. By virtue of the cells being screened from the immune system, it is possible to implant in a patient cells which are foreign to the body and which over a relatively long period of time discharge a desired substance into the body of the patient without the cells being attacked and destroyed by the patient's immune system.

Encapsulation of cells and catalysts in biopolymers—such as carrageenan or alginate—and synthetic polymers—such as polyacrylamide—is a method which has been used for some years in research laboratory situations. Many different apparatuses are described for that purpose in the literature. One of the most efficient methods involves dividing up a jet by the superimposition of an external vibration on the immobilisation fluid. The fluid is thereby divided into fractions of equal size as it issues in a laminar flow from a nozzle. A number of methods for the transmission of vibration are used or described, for example coupling to a vibrator, piezoelectric crystal, sound waves.

WO 96/28247 to the present applicants discloses a commercial encapsulation unit in which the vibration is transmitted by a rigid connection to a vibrator. That method suffers from the difficulty that the axis of the vibrator and the axis of the nozzle have to be exactly aligned as otherwise disturbances occur, which massively adversely affect the homogeneity of the sphere size. The vibrator is also expensive. In addition, it has been found by photographic analysis procedures and observations under stroboscope light that, in regular operation of the apparatus, a monodisperse and single-strand chain of spheres is visible to about 100 mm downstream of the nozzle. If the spheres are caught after about 100 mm dropping distance in a hardening bath and are thereafter examined under a microscope, then very often batches without a monodisperse group of spheres is obtained—and this was not predictable. The samples generally had three different sphere populations in a varying ratio; the first was of the expected sphere diameter, the second was of double or a multiple greater volume than expected, and the third was in the form of two individual spheres which touch each other to a greater or lesser degree.

In consideration of that state of the art the inventor set himself the aim of optimising an apparatus and a method of the kind set forth in the opening part of this specification.

That object is attained by the teachings of the independent claims; the appendant claims set forth advantageous developments. In addition the scope of the invention embraces all combinations of at least two of the features disclosed in the description, the drawing and/or the claims.

In accordance with the method according to the invention the immobilisation mixture, in particular a laminar fluid jet, is separated into parts of equal size by the superimposition of an external vibration. An electrical field is built up in the proximity of the nozzle so that an electrical charge flux occurs in the fluid jet, whereby the drops produced have an electrical charge. That charge must be so high that the spheres mutually repel because of the similar charge and the chain of spheres which is initially present in the form of a single strand is divided into many partial chains. For that purpose, voltages are required which are preferably in the range of between 200 and 1600 V. Due to the dispersing effect, the spheres no longer drop on a closely defined region on to the surface of the hardening bath, but they are scattered far and wide.

In that way it is now possible as a routine matter to obtain a monodisperse sphere array not only in the air but also in the hardening bath. Likewise, in the case of immobilisation mixtures which by virtue of their chemical and physical properties could be scarcely or only partially put into drop form, it is now also often possible to achieve a monodisperse sphere assembly.

An apparatus which is intended for that method is distinguished inter alia in that a metal counterpart element which is arranged downstream of the nozzle at a spacing and outside the nozzle axis is connected to a high-voltage source. That counterpart element is preferably in the form of a metal ring having an aperture through which the nozzle axis was to pass. Provided between the nozzle and the counterpart element or metal ring is an electrical field, preferably with the above-mentioned voltage range.

It has also proven to be advantageous, when dividing the immobilisation mixture by the superimposition of an external vibration into fractions of equal size, for those vibrations to be transmitted to the immobilisation mixture either within a pulsation space or chamber or by way of the nozzle which is caused to pulsate. Provided for that purpose is an apparatus in which a pulsation chamber which is arranged upstream of the nozzle and which receives the immobilisation mixture has a permanent magnet superimposed thereon and the permanent magnet is arranged opposite an electrical coil; in accordance with the invention one of the two units is provided within the pulsation chamber or on a diaphragm which extends over the pulsation chamber, while the other unit is separated by an air gap from that which is associated with the pulsation chamber.

In another embodiment of the apparatus the permanent magnet and the electrical coil are associated with the nozzle or the suspension thereof so that same can initiate the pulsation procedure.

The principle of the vibrator comprising the magnet and a coil through which alternating current flows is taken from the vibrator, and a part thereof is directly associated with the pulsation chamber. When alternating current is passed through the coil, it is alternately magnetised positively and negatively. The magnetic waves interact with the subjacent magnet and cause it to vibrate. The vibrations are transmitted almost without resistance to the immobilisation fluid.

In accordance with a further feature of the invention the coil through which alternating current flows and the permanent magnet produce vibrations in the preferred range of between 300 and 4000 Hz.

Thus using simple means the invention permits miniaturisation of vibration transmission, with a very low level of expenditure in terms of material and energy. The costs of the method and the apparatus can be reduced by a multiple in comparison with the previously known vibration methods. A further advantage to be considered here is that the orientation of the magnet and the coil does not have to be centered to an accuracy of 0.1 mm. There are also no axes which have to be precisely oriented.

Further advantages, features and details of the invention will be apparent from the description hereinafter of preferred embodiments and with reference to the drawing in which.

Figure 1:
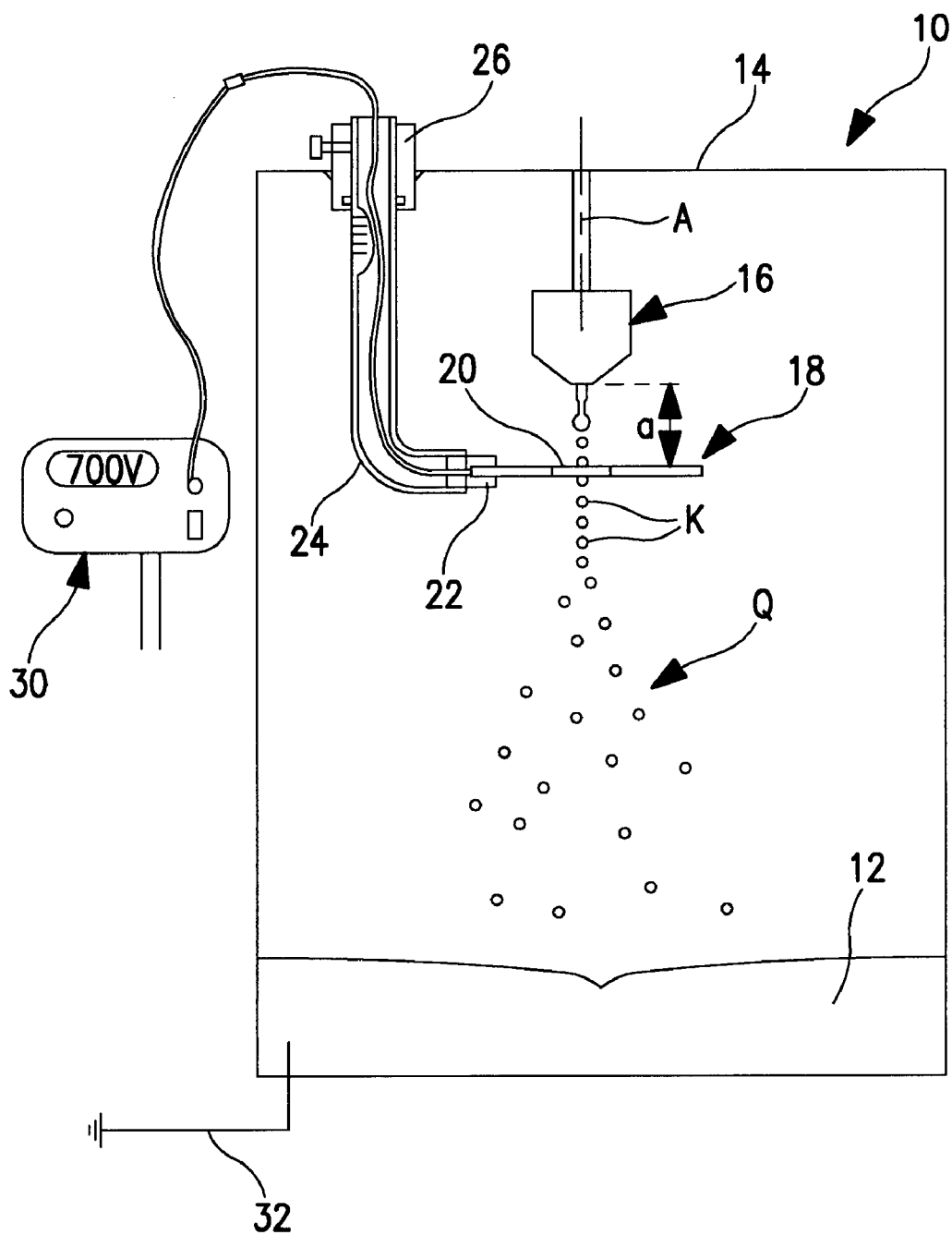
FIG. 1 is a side view of an apparatus according to the invention.
Figure 2:
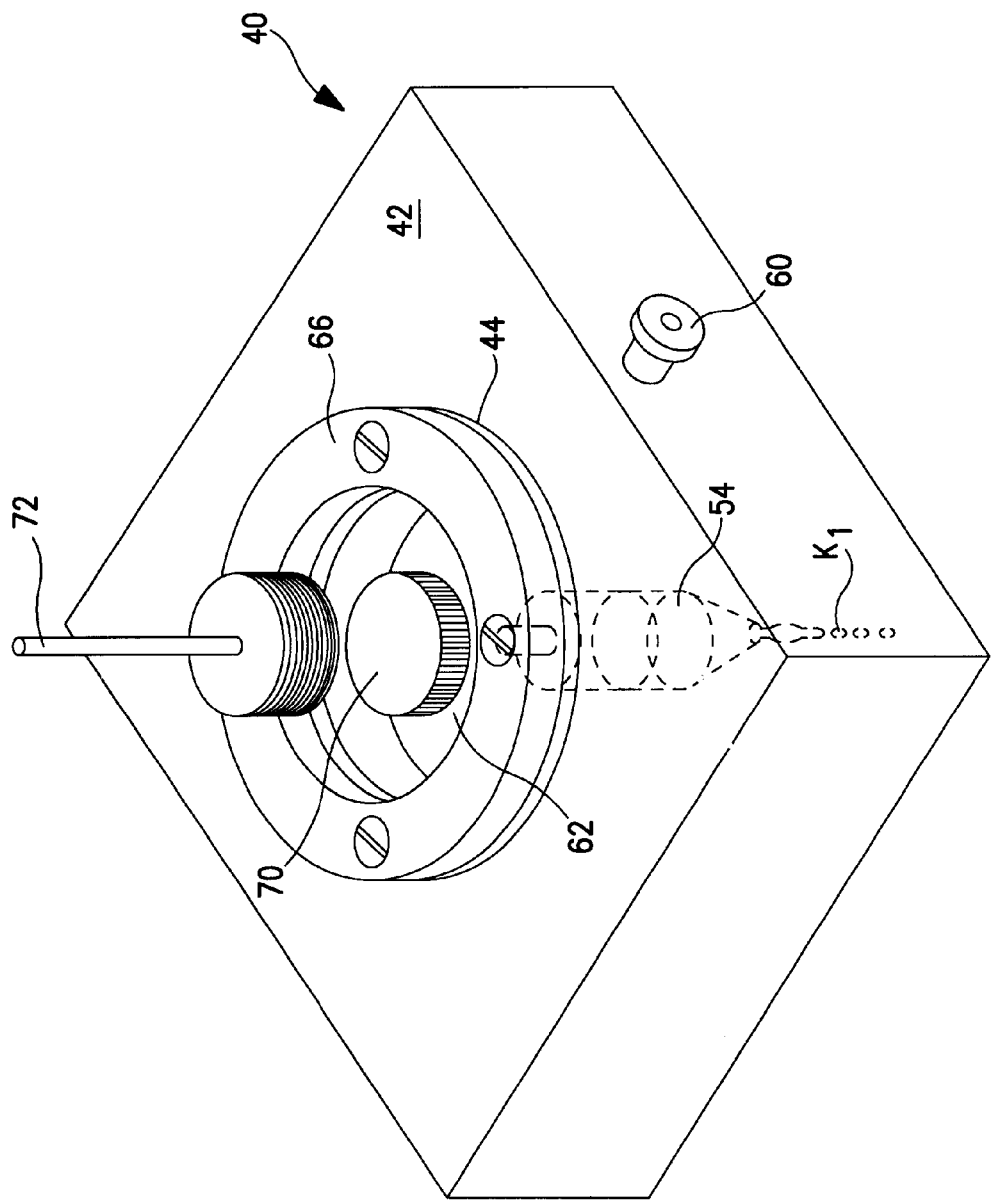
FIG. 2 is a perspective view of another apparatus according to the invention.
Figure 3:
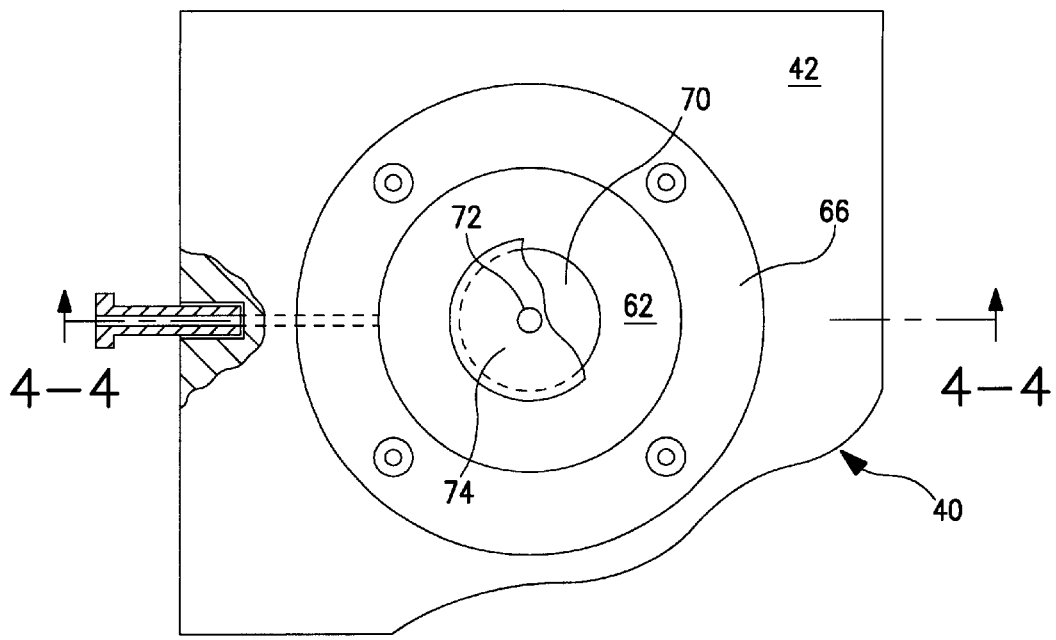
FIG. 3 is a plan view of the partly sectioned apparatus in FIG. 2.

In an installation of which only part is shown for the sterile encapsulation of microbial, vegetable and animal cells, disposed horizontally in a reactor 10 above a hardening bath 12 and below a nozzle 16 which is suspended from a reactor cover 14 and at a spacing a in relation to the nozzle 16 is a metal ring 18 having a central aperture 20 through which the nozzle axis A passes.

The metal ring 18 is secured by means of a radial holder 22 and a tube 24 connected thereto in an insulating connection portion 26 in the reactor cover 14 and is connected through a line 28 disposed in the tube 26 to a high-voltage source 30.

An encapsulation mixture comprising an immobilisation matrix and cells or substances is conveyed through the nozzle 16 in such a way that a free laminar jet is produced. By virtue of a vibration being superimposed on the free jet, the free jet is broken up into drops K of equal size. When the fluid penetrates into an electrical field which is built up between the metal ring 18 and the nozzle 16, a charge flux occurs in the direction of the nozzle 16 so that the separated drops K have an electrical charge, being an electrostatic charge. That similar charge causes mutual repulsion of the drops K.

That procedure results in two effects. On the one hand, the drops K are stabilised in the axial direction, that is to say as soon as two drops K come closer together by virtue of different speeds of fall, they are repelled by the coulomb forces and they cannot come into contact with each other. On the other hand, very small radial displacements are increased and the single-strand chain of spheres is expanded to form a cone Q. Due to that effect, coagulation of drops K is practically prevented and particles of completely equal size are produced in the hardening bath 12. The charges are removed by grounding of the hardening bath 12 at 32.

In an embodiment of a further installation for sterile encapsulation of microbial, vegetable and animal cells, arranged above the hardening bath 12 is a carrier plate 40 of a thickness b, which for example is rectangular, with a depression 44 of a depth t which is formed in the center of its surface 42; the depth t corresponds approximately to one third of the plate thickness b.

Figure 4:
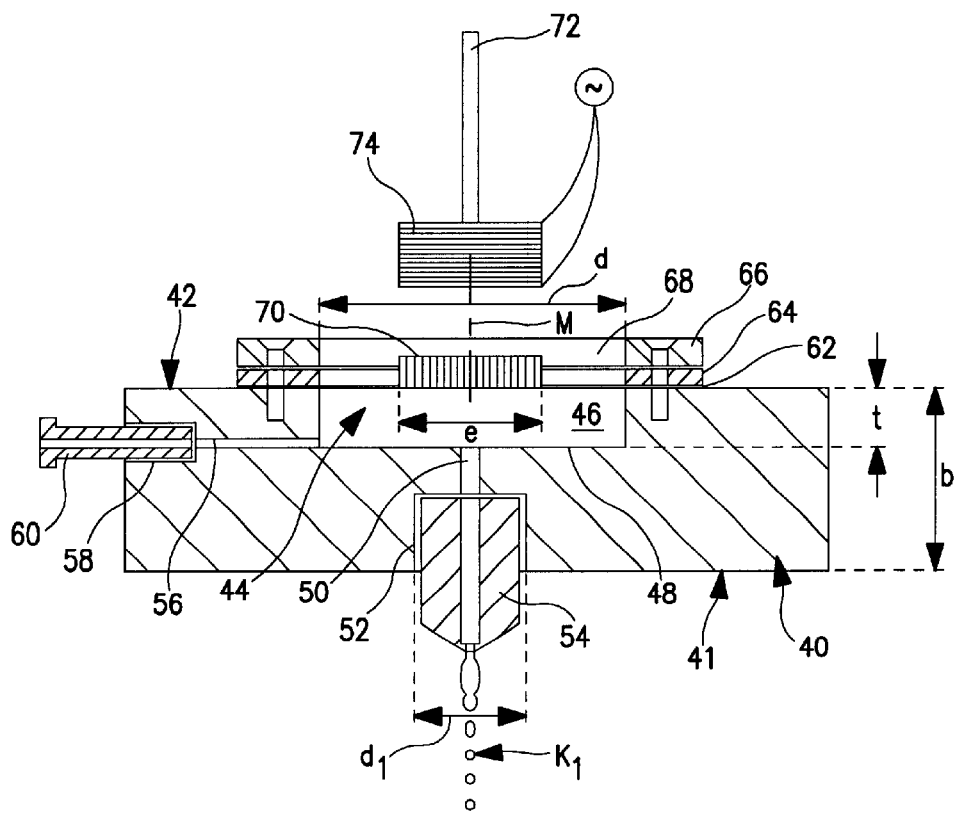
FIG. 4 is a view in section through FIG. 3 taken along line IV—IV therein.

The depression 44, as shown in FIG. 4, is defined by a circular peripheral wall 46 of a diameter d, and a bore 50 extends from the center point of its bottom 48. The bore 50 opens at the other end in a cup-shaped recess 52 of a diameter $d_1$ (approximately one third of d), which is provided in the underneath surface 41 of the carrier plate 40 and in which is carried a nozzle 54 connected to the bore 50. In addition, in the plane of the bottom 48, a radial passage 56 leads to a lateral blind hole 58 for a connecting portion 60.

Associated with the depression is a pressure ring 66 which is fixed on the plate surface 42 with the interposition of a diaphragm 62 and a seal 64; the pressure ring 66, like also the seal 64, is provided with an internal aperture 68 of a diameter d and the diaphragm 62 which carries a disk magnet 70 extends over the depression 44. The diameter e of the magnet 70 is somewhat greater than the diameter $d_1$ of the recess 52 for the nozzle 54.

An electrical coil 74 is suspended from a holder 72 at a spacing with respect to the disk magnet 70, centered with respect to the center line M thereof. The disk magnet 70 and the coil 74 through which alternating current flows form a vibrator; when alternating current is passed through the coil 74 it is alternately positively and negatively magnetised. The magnetic waves act on the subjacent disk magnet 70 and cause it to vibrate together with the diaphragm 62.

An immobilisation fluid is introduced through the radial passage 56 into the depression 44 which forms a pulsation chamber, the vibrations being transmitted almost without resistance to the immobilisation fluid. The introduction of that immobilisation mixture is effected by means of a mechanical feed thrust or by air pressure into the pulsation chamber or recess 44; from there the immobilisation mixture is urged through the nozzle 54. The jet E which is produced there, shortly after issuing from the nozzle 54, breaks up into spheres $K_1$ of equal size, according to the frequency of the superimposed vibration. At about 700 Hz, under optimum conditions, 700 of the equal-sized spheres $K_1$ are produced per second, while the homogeneity of the sphere configuration is excellent by virtue of the friction-less transmission. Measurements have shown that the power required is less than 0.2 W.

In an embodiment not shown herein the permanent magnet 70 or the coil 74 is provided directly at the nozzle 54 and the respective other unit is associated therewith, forming an air gap.

What is claimed is:

1. A method for encapsulating an immobilization mixture comprising the steps of:

providing a stream of an immobilization mixture;

vibrating the stream wherein the stream is formed into drops by the vibration;

subjecting the drops to a magnetic fluid wherein the drops are electrically charged thereby resulting in mutual repulsion; and passing the charged drops to a hardening bath for encapsulating.

2. A method as set forth in claim 1, wherein immobilization mixture is divided into fractions of equal size by the vibration.

3. A method as set forth in claim 1, wherein the vibration is transmitted to the immobilization mixture within a pulsation chamber.

4. A method as set forth in claim 1, wherein vibration is transmitted to the immobilization mixture by way of the nozzle which is caused to pulsate.

5. A method as set forth in claim 1, wherein the vibration is in the range of between 300 and 4000 Hz.

6. A method as set forth in claim 1, wherein the drops form a cone beneath the magnetic field and above the hardening bath.

7. A method as set forth in claim 1, wherein the electrical voltage of the magnetic field is in the range of between 200 and 1600 V.

8. A method for encapsulating an immobilization mixture comprising the steps of:

providing a nozzle;

providing a ring having an aperture in line with the nozzle downstream of the nozzle at a distance "a";

providing a magnetic field between the nozzle and the ring;

vibrating the ring; and passing the immobilization mixture from the nozzle, through the magnetic field and the aperture in the vibrating ring whereby the immobilization mixture is formed by vibration into drops having an electrical charge which results into mutual repulsion of the drops.

9. An apparatus for encapsulating an immobilization mixture comprises:

a nozzle having an outlet;

a metal ring positioned beneath the nozzle a distance "a", the metal ring having an aperture in line with the outlet of the nozzle; and a high voltage source connected to the metal ring.

10. An apparatus as set forth in claim 9, wherein the high voltage source creates an electrical field between the nozzle and the metal ring of an electrical voltage in the range of between 200 and 1600 V.

11. An apparatus as set forth in claim 9, wherein the metal ring is radially connected to an insulatedly mounted holder.

12. An apparatus as set forth in claim 9, wherein a pulsation chamber is arranged upstream of the nozzle and receives the immobilization mixture, a permanent magnet acts on the pulsation chamber and is arranged opposite an electrical coil.

* * * * *